US008882814B2

(12) United States Patent
Suh

(10) Patent No.: US 8,882,814 B2
(45) Date of Patent: Nov. 11, 2014

(54) ORTHOPEDIC PLATING ASSEMBLY FOR BONE FIXATION AND SUBSIDENCE

(75) Inventor: Sean Suh, Plymouth Meeting, PA (US)

(73) Assignee: Globus Medical, Inc., Audubon, PA (US)

( * ) Notice: Subject to any disclaimer, the term of this patent is extended or adjusted under 35 U.S.C. 154(b) by 208 days.

(21) Appl. No.: 12/698,412

(22) Filed: Feb. 2, 2010

(65) Prior Publication Data

US 2011/0190770 A1    Aug. 4, 2011

(51) Int. Cl.
*A61B 17/80*      (2006.01)
(52) U.S. Cl.
CPC .................................... *A61B 17/80* (2013.01)
USPC ............ 606/289; 606/286; 606/295; 606/280
(58) Field of Classification Search
USPC ...................................... 606/70, 71, 280–299
See application file for complete search history.

(56) References Cited

U.S. PATENT DOCUMENTS

| | | | |
|---|---|---|---|
| 5,549,612 A * | 8/1996 | Yapp et al. ..................... 606/293 |
| 5,951,558 A * | 9/1999 | Fiz ................................... 606/70 |
| 6,152,927 A * | 11/2000 | Farris et al. ................... 606/287 |
| 6,193,721 B1 * | 2/2001 | Michelson ...................... 606/70 |
| 6,503,250 B2 * | 1/2003 | Paul .............................. 606/279 |
| 7,115,130 B2 * | 10/2006 | Michelson ...................... 606/71 |
| 8,062,367 B2 * | 11/2011 | Kirschman ................ 623/17.11 |
| 2004/0102776 A1 * | 5/2004 | Huebner ......................... 606/69 |
| 2004/0220572 A1 * | 11/2004 | Michelson ...................... 606/71 |
| 2005/0261690 A1 * | 11/2005 | Binder et al. .................. 606/69 |
| 2010/0292696 A1 * | 11/2010 | Chantelot et al. .............. 606/70 |

FOREIGN PATENT DOCUMENTS

FR      2006001265     *   6/2006       A61B 17/80

* cited by examiner

*Primary Examiner* — Matthew Lawson
*Assistant Examiner* — Si Ming Lee

(57) ABSTRACT

In an exemplary embodiment, the present invention provides an orthopedic plating assembly for bone fixation that includes an orthopedic plate and orthopedic anchors that can accommodate subsidence in the vertebral bodies as well as prevent the anchors from "backing out" of their installed position. The assembly, in one embodiment, includes an orthopedic plate and at least one orthopedic anchor, the orthopedic anchor capable of rotating and translating with respect to the plate. The assembly further includes a first blocking member and a second blocking member, the blocking members cooperate to prevent the at least one orthopedic anchor from uninstalling from an installed position.

16 Claims, 2 Drawing Sheets

ORTHOPEDIC PLATING ASSEMBLY FOR BONE FIXATION AND SUBSIDENCE

FIELD OF THE INVENTION

The present invention is generally directed to an orthopedic plating assembly used for bone fixation and subsidence. In particular, the present invention relates to a plating assembly capable of blocking orthopedic anchors to prevent the anchor from disengaging or dislodging from the orthopedic implant.

BACKGROUND OF THE INVENTION

Whether to treat degenerative disease, traumatic injury, or defect, congenital or otherwise, surgical reconstructions of bony elements are common procedures in current medical practice. Regardless of anatomical region or the specifics of the reconstructive procedure, many surgeons employ orthopedic devices or implants to adjust, align and maintain the spatial relationships of adjacent bones or bony fragments during postoperative osteosynthesis. With respect to surgical reconstruction in the spinal region, it is known to employ orthopedic plates to adjust, align and maintain the spatial relationship of adjacent vertebral bodies to promote postoperative fusion. It is further known to attach the orthopedic plate to the vertebral bodies using orthopedic anchors which act to share the load and support the bone and orthopedic plate as fusion progresses.

In some cases, subsidence occurs in the bone or bone fragments to which the orthopedic plate and anchors are attached. The definition of subsidence in terms of spinal biomechanics is the sinking of the orthopedic plate and anchors having a higher elasticity modulus in one or more vertebral bodies characterized by a lower elasticity modulus, resulting in changes of the spinal geometry. Any excessive subsidence decreases the interbody space and produces both local and general kyphotization of the spine which can cause destabilization of the screw-plate and/or screw-bone interfaces (e.g. pulling-out, altered angulation or breakage of the screws).

In addition, notwithstanding the forces resulting from subsidence, over time, it has also been found that as a result of the forces placed upon the orthopedic device and anchors resulting from the movement of the spine, the orthopedic anchors can begin to back out from their installed position eventually resulting in the anchors disconnecting from the device.

As such, there exists a need for an orthopedic plate and anchors that can accommodate subsidence in the vertebral bodies as well as prevent the fasteners from "backing out" of their installed position.

SUMMARY OF THE INVENTION

In one embodiment, the present invention provides an orthopedic plating assembly for bone fixation that includes an orthopedic plate and orthopedic anchors that can accommodate subsidence in the vertebral bodies as well as prevent the anchors from "backing out" of their installed position. The assembly, in one embodiment, includes an orthopedic plate and at least one orthopedic anchor, the orthopedic anchor capable of rotating and translating with respect to the plate. The assembly further includes a first blocking member and a second blocking member, the blocking members cooperate to prevent the at least one orthopedic anchor from uninstalling from an installed position.

Further areas of applicability of the present invention will become apparent from the detailed description provided hereinafter. It should be understood that the detailed description and specific examples, while indicating the preferred or exemplary embodiments of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

The following description of the preferred embodiment(s) is merely exemplary in nature and is in no way intended to limit the invention, its application, or uses.

With reference to FIGS. 1-4, an embodiment of an orthopedic plating assembly 10 is illustrated. Although the assembly 10 is shown isolated from the environment it would typically be used in, it should be understood that the assembly 10 provides a bone fixation and/or fusion solution with an orthopedic plate and orthopedic anchors that can accommodate subsidence in the vertebral bodies and can prevent the anchors from "backing out" of their installed position via an anchor blocking system. Further, it should be understood that the assembly 10, although disclosed as being used on the spine with respect to vertebral bodies, can also be used on any appropriate bony anatomical region and with any appropriate reconstructive procedure.

Figure 1:
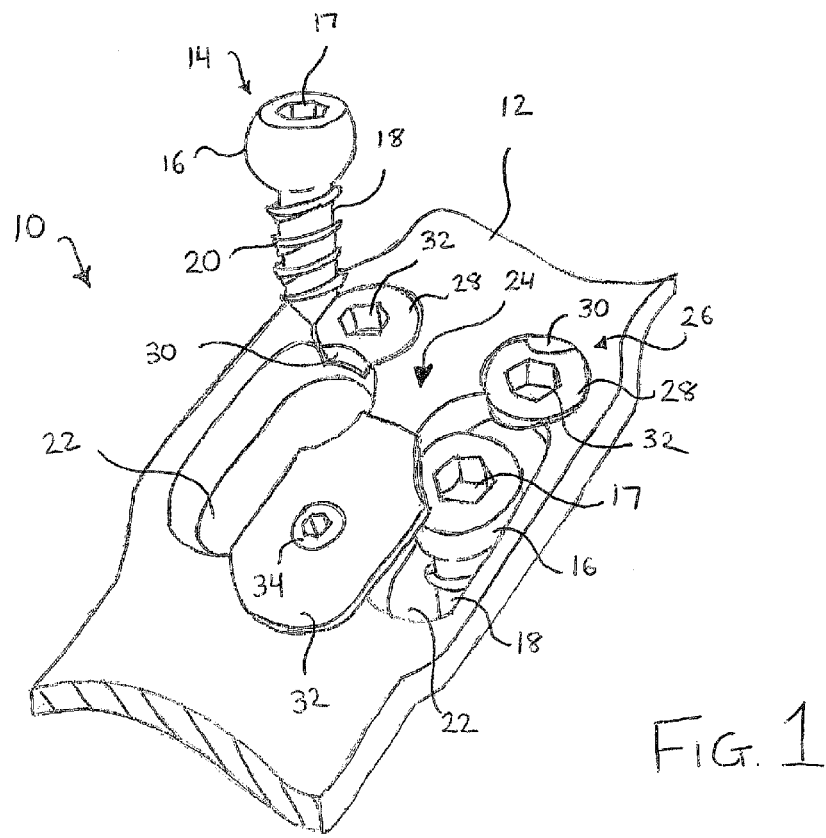
FIG. 1 is a partial perspective view of one embodiment of an orthopedic plating assembly.

The assembly 10 preferably includes an orthopedic plate 12 and at least one anchor 14 having a head portion 16, a shank portion 18, and threads 20 that surround at least a portion of the shank portion 18. The head portion 16, preferably, is, at least in part, generally spherical and includes an opening 17 for receiving an instrument capable of engaging and driving the anchor 14 into bone tissue 1. Although only one anchor is discussed, as shown in FIG. 1, two anchors 14 can be included in the assembly and it is further contemplated that the assembly 10 can include any number of anchors.

Figure 4:
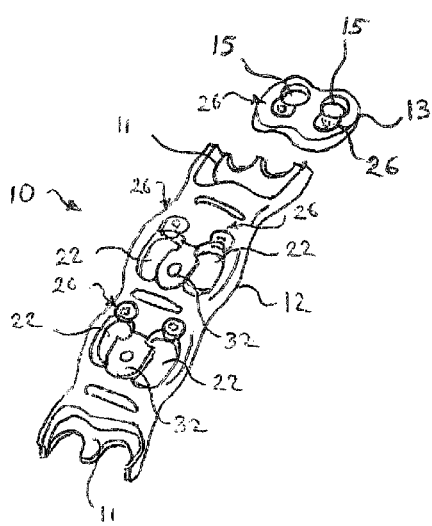
FIG. 4 is a perspective view of the orthopedic plating assembly of FIG. 1.

In a preferred embodiment, as shown in FIG. 4, the plate 12 includes carriage plates 13 at one or both ends of the plate 12. The carriage plates 13 include at least one opening 15 for receiving an anchor 14. The openings 15 are preferably configured and dimensioned to approximate the dimensions of the head portion 16. This dimensioning of openings 15 will permit the anchors 14, when in an installed position, to rotate in a poly-axial fashion with respect to the carriage plate 13 providing rigid fixation of the carriage plate 13 to the anchor 14 and bone tissue. Furthermore, although captured in the slots 11 of plate 12, the carriage plates 13 can slide with respect to the plate 12 allowing the plate 12 to translate after being fastened to the bone tissue 1.

In a preferred embodiment, the plate 12 also includes at least one opening 22 for each anchor 14. The openings 22 are elongated, as best seen in FIG. 1, permitting the anchors 14, when in an installed position, to translate and rotate in a poly-axial fashion with respect to the plate 12. This translatability and rotational freedom coupled with the slidable carriage plates 13 provides additional functionality as the assembly 10 can continue to function effectively even under bone subsidence conditions. For example, if subsidence were to occur in the vertebral bodies to which the assembly 10 has been fastened, the plate 12, the carriage plate 13, and anchors 14 can move with respect to each other, in a rotational as well as translational fashion, to accommodate the subsidence without destabilizing the anchor-plate and/or anchor-bone interfaces. Alternatively, it is also contemplated that the openings 22, rather than being elongated, can be configured and dimensioned to approximate the dimensions of the head portion 16. This dimensioning of opening 22 will prevent the anchors 14 from translating but will still permit the anchors 14 to rotate in a poly-axial fashion with respect to the plate 12 providing rigid fixation of the orthopedic plate 12 to the anchor 14 and bone tissue 1.

In a preferred embodiment, the assembly 10 also includes a blocking mechanism 24. The blocking mechanism 24 preferably is comprised of two components that cooperate to block the anchors 14 from backing out or otherwise disengaging from the orthopedic plate 12 after installation of the assembly 10. The first component is a blocking screw 26 having an enlarged head 28. It is contemplated that there will be at least one blocking screw 26 adjacent each opening 22 and each opening 15. In a preferred embodiment, the head 28 includes a cutout 30 and an opening 32 for receiving an actuation instrument. As discussed further below, the orientation of cutout 30 with respect to the opening 22 and opening 15 will determine whether the head 28 is in a blocking position or a non-blocking position. Although the blocking screw 26 is shown as being a set screw, any mechanism that would serve as a blocking mechanism is contemplated, such as a cam type mechanism or a slideable interference mechanism.

Figure 2:
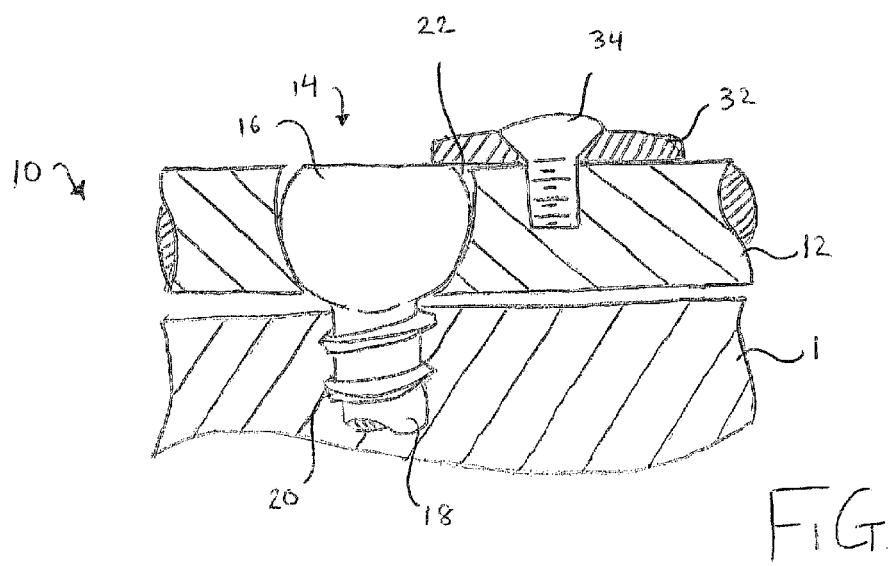
FIG. 2 is a partial cross-sectional side view of the orthopedic plating assembly of FIG. 1.

The second component is a blocking plate 32. As shown in FIGS. 1, 2 and 4, the blocking plate 32 is preferably removable connected to the plate 12 and is shaped and dimensioned to block at least a portion of at least one opening 22. In a preferred embodiment, as best seen in FIG. 4, it can be seen that there is one blocking plate 32 for each pair of elongated openings 22. The blocking plate 32 is connected to the plate 12 via a screw. Preferably, both the blocking plate 32 and the screw 34 have a low-profile thereby not increasing the overall thickness of the orthopedic plate 12. The blocking plate 32 can be installed prior to the introduction of the anchors 14 or can be installed after the anchors 14 have been installed through the openings 22.

In an exemplary use of the assembly 10 as shown in FIG. 4, the plate 12 is placed on or near the area of treatment. The anchors 14 are installed through the openings 15, 22 from a first uninstalled position to a second installed position where the anchors 14, in the installed position, engage the plate 12 and the carriage plate 13 as well as the anatomy in the area of treatment to secure the plate 12 in place. With respect to the anchors 14 that are installed through the openings 15, after the anchors 14 are installed in place, the blocking screw 26 is manipulated via opening 22 so that the enlarged head portion 28 blocks anchor 14 from backing out or from moving in an direction opposite from the direction of installation. This is accomplished by moving the cutout 30 from facing the opening 22 to a position where the cutout 30 is not facing the opening 22. With the cutout 30 oriented away from the opening 15, there is no longer enough room for the anchor 14 to pass back through the opening 15 thereby preventing the anchors 14 from "backing out."

Figure 3A:
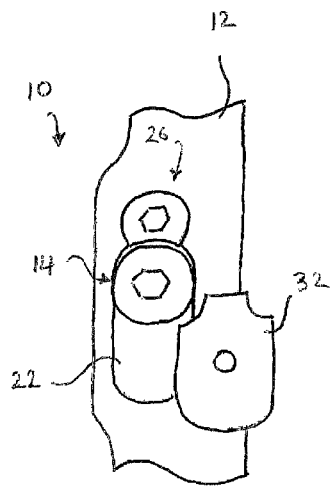
FIGS. 3A-3C are schematic top views of the assembly shown in FIG. 1 showing the orthopedic anchor in various positions with respect to the orthopedic plate.
Figure 3B:
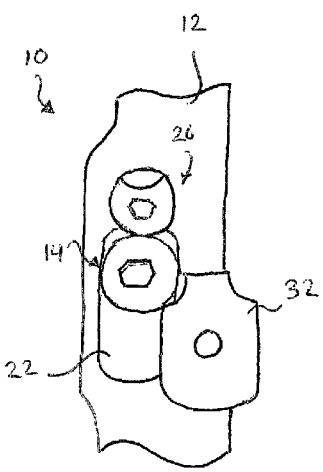
Figure 3C:
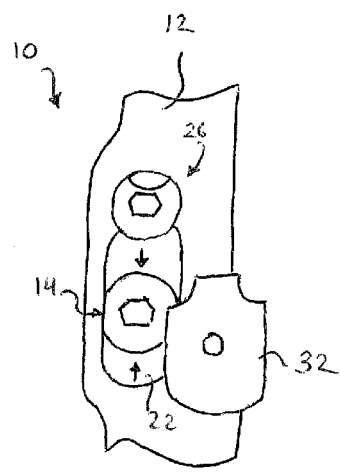

With respect to the anchors 14 that are installed through the openings 22, as best seen in FIG. 3A, the anchors 14 are installed through portions of the openings 22 that are not covered by the blocking plate 32. After the anchors 14 are installed in place, the blocking screw 26 is manipulated via opening 32 so that the enlarged head portion 26 blocks anchor 14 from backing out or from moving in a direction opposite from the direction of installation. This is accomplished by moving the cutout 30 from facing the opening 22 to a position where the cutout 30 is not facing the opening 22. This position of cutout 30 can best be seen in FIGS. 3B and 3C. With the cutout 30 oriented away from the opening 22, there is no longer enough room between the head 28 of blocking screw 26 and the covering plate 32 for the anchor 14 to pass through. Accordingly, once the anchors 14 are installed in place, the manipulation of blocking screw 26 coupled with the blocking plate 32 prevents those anchors 14 from "backing out." Furthermore, even if the plate 12 were to translate with respect to the anchors 14, as seen in FIGS. 3B and 3C, the anchors 14 will still be prevented from backing out by virtue of the blocking plate 32 covering at least a portion of the openings 22.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. An orthopedic plate assembly for bone fixation, comprising:
   at least one orthopedic anchor having a head portion;
   an orthopedic plate having an upper surface, a lower surface and at least one opening that extends between the upper surface and the lower surface, the at least one opening configured and dimensioned to receive the orthopedic anchor;
   a first blocking member including a cut-out portion, the first blocking member having a blocking position and a non-blocking position, the first blocking member being rotatable from the non-blocking position to the blocking position, wherein in the non-blocking position the cut-out portion faces the orthopedic anchor and in the blocking position, the cut-out portion faces away from the orthopedic anchor; and
   a second blocking member, the second blocking member removably connected to the orthopedic plate and positioned to cover at least a portion of the opening, wherein the second blocking member rests above an uppermost surface of the orthopedic plate,
   wherein the orthopedic anchor is able to pivot and laterally translate with respect to the orthopedic plate when in an installed position in the opening, and
   wherein the first blocking member and the second blocking member cooperate to prevent the at least one orthopedic anchor from uninstalling from the plate when the first blocking member is in the blocking position, wherein the second blocking member comprises a top surface, a bottom surface and sidewalls between the top surface and the bottom surface, such that rotation of the first blocking member causes the orthopedic anchor to be bounded by a sidewall of the first blocking member and the bottom surface of the second blocking member.

2. The assembly of claim 1, further comprising at least one carriage plate, the at least one carriage plate having at least one opening for receiving at least one orthopedic anchor.

3. The assembly of claim 2, wherein the orthopedic plate has at least one slot and wherein the at least one carriage plate is slideably received in the slot of the orthopedic plate.

4. The assembly of claim 3, wherein the at least one carriage plate is captured in the slot of the orthopedic plate.

5. The assembly of claim 2, wherein the at least one carriage plate has at least one blocking member having a blocking position and a non-blocking position.

6. The assembly of claim 1, wherein the opening is elongated.

7. The assembly of claim 1, wherein the first blocking member includes an enlarged head portion and a cutout portion.

8. The assembly of claim 7, wherein first blocking member is rotatable from the blocking position where the head portion faces the opening of the orthopedic plate to the unblocking position where the cutout portion faces the opening in the orthopedic plate.

9. The assembly of claim 1, wherein the second blocking member is removably connected to the orthopedic plate which includes at least one set screw.

10. The assembly of claim 1, wherein the orthopedic anchor has a head portion, a shank portion, and threads that surround at least a portion of the shank portion and wherein the head portion is in part spherical and includes an opening for receiving an instrument capable of engaging and driving the anchor into bone tissue.

11. An orthopedic plate assembly for bone fixation, comprising:
  at least one orthopedic anchor having a head portion;
  an orthopedic plate having an upper surface, a lower surface and at least one opening that extends between the upper surface and the lower surface, the at least one opening configured and dimensioned to receive the orthopedic anchor;
  a first blocking member, the first blocking member having a blocking position and a non-blocking position; and
  a second blocking member, the second blocking member removably connected to the orthopedic plate and positioned to cover at least a portion of the opening, wherein the orthopedic anchor is able to pivot and laterally translate with respect to the orthopedic plate when in an installed position in the opening,
  wherein a sidewall of the first blocking member contacts a sidewall of the head portion of the at least one orthopedic anchor when the first blocking member is rotated from the non-blocking position to the blocking position, wherein the second blocking member comprises a top surface, a bottom surface and sidewalls between the top surface and the bottom surface, such that rotation of the first blocking member causes the orthopedic anchor to be bounded by a sidewall of the first blocking member and the bottom surface of the second blocking member.

12. The assembly of claim 11, further comprising at least one carriage plate, the at least one carriage plate having at least one opening for receiving at least one orthopedic anchor.

13. The assembly of claim 12, wherein the orthopedic plate has at least one slot and wherein the at least one carriage plate is slideably received in the slot of the orthopedic plate.

14. The assembly of claim 13, wherein the at least one carriage plate is captured in the slot of the orthopedic plate.

15. The assembly of claim 12, wherein the at least one carriage plate has at least one blocking member having a blocking position and a non-blocking position.

16. An orthopedic plate assembly for bone fixation, comprising:
  at least one orthopedic anchor having a head portion;
  an orthopedic plate having an upper surface, a lower surface and at least one opening that extends between the upper surface and the lower surface, the at least one opening configured and dimensioned to receive the orthopedic anchor;
  a first blocking member, the first blocking member having a head, the first blocking member having a blocking position and a non-blocking position; and
  a second blocking member, the second blocking member removably connected to the orthopedic plate and positioned to cover at least a portion of the opening, wherein the second blocking member rests above an uppermost surface of the orthopedic plate,
  wherein the orthopedic anchor is able to pivot and laterally translate with respect to the orthopedic plate when in an installed position in the opening,
  wherein at least a portion of a side of the head of the first blocking member is in a same plane as the head portion of the orthopedic anchor so as to restrict lateral translation of the orthopedic anchor,
  wherein an upper most surface of the second blocking member has a distance of separation from the plate that is greater than a distance of separation between an uppermost surface of the first blocking member and the plate in the installed position,
  wherein a sidewall of the first blocking member contacts a sidewall of the head portion of the at least one orthopedic anchor when the first blocking member is rotated from the non-blocking position to the blocking position
  wherein the first blocking member does not cover the top surface of the head portion of the at least one orthopedic anchor when the first blocking member is in a blocking position, wherein the second blocking member comprises a top surface, a bottom surface and sidewalls between the top surface and the bottom surface, such that rotation of the first blocking member causes the orthopedic anchor to be bounded by a sidewall of the first blocking member and the bottom surface of the second blocking member.

* * * * *